(12) United States Patent
Cocker et al.

(10) Patent No.: US 12,064,547 B2
(45) Date of Patent: Aug. 20, 2024

(54) DRY POWDER INHALER DEVICE

(71) Applicant: PHILIP MORRIS PRODUCTS S.A., Neuchâtel (CH)

(72) Inventors: Robin Craig Cocker, Derby (GB); Christopher Iain Davidson, Cambridge (GB); Steve Han, Huntington Beach, CA (US); Ben Alexander King, Oundle (GB); Paul Mutti, Spilsby (GB); Alex Stenzler, Long Beach, CA (US); James Tibbatts, Cambridge (GB)

(73) Assignee: Philip Morris Products S.A., Neuchâtel (CH)

( * ) Notice: Subject to any disclaimer, the term of this patent is extended or adjusted under 35 U.S.C. 154(b) by 618 days.

(21) Appl. No.: 17/422,797

(22) PCT Filed: Jan. 13, 2020

(86) PCT No.: PCT/IB2020/050232
§ 371 (c)(1),
(2) Date: Jul. 14, 2021

(87) PCT Pub. No.: WO2020/148631
PCT Pub. Date: Jul. 23, 2020

(65) Prior Publication Data
US 2022/0126034 A1    Apr. 28, 2022

(30) Foreign Application Priority Data
Jan. 14, 2019 (EP) .................................... 19151681

(51) Int. Cl.
*A61M 15/00* (2006.01)
*A24F 42/20* (2020.01)
*A24F 42/60* (2020.01)

(52) U.S. Cl.
CPC ......... *A61M 15/0023* (2014.02); *A24F 42/20* (2020.01); *A24F 42/60* (2020.01); *A61M 15/0066* (2014.02); *A61M 2202/064* (2013.01)

(58) Field of Classification Search
CPC ... A24F 42/20–60; A61M 15/00–0001; A61M 15/0005; A61M 15/0021–0023; A61M 15/0065–0066
See application file for complete search history.

(56) References Cited

U.S. PATENT DOCUMENTS 6,234,169 B1    5/2001  Bulbrook et al.
2005/0103336 A1*  5/2005  Nishibayashi .... A61M 15/0075
                                                    128/203.11

(Continued)

FOREIGN PATENT DOCUMENTS

CA    2706569 A1    5/2009
EP    0407028        3/1991

(Continued)

OTHER PUBLICATIONS

International Preliminary Report on Patentability for PCT/IB2020/050232, issued Jul. 29, 2021; 7 pages.

(Continued)

*Primary Examiner* — Rachel T Sippel
(74) *Attorney, Agent, or Firm* — Mueting Raasch Group

(57) ABSTRACT

Dry powder inhalers are described. The dry powder inhaler includes an air inlet, a reservoir and an airway assembly. A mouthpiece airway is connected to a first airway of the airway assembly. An airway head is attached to the airway assembly and it extends into the reservoir cavity. In certain embodiments, the airway head has a sharpened or beveled edge. At least one airway assembly opening is present in the airway assembly for connecting the reservoir cavity to the first airway. Methods for dispensing dry powder into an airway of a dry powder inhaler and inhaling dry powder (Continued)

from a dry powder inhaler is also disclosed. Embodiments of a dry powder inhaler having a two-stage air movement are also described.

20 Claims, 15 Drawing Sheets

(56) References Cited

U.S. PATENT DOCUMENTS

| | | | |
|---|---|---|---|
| 2010/0258118 A1* | 10/2010 | Morton | A61M 15/0078 |
| | | | 264/9 |
| 2018/0021529 A1 | 1/2018 | Tibbatts et al. | |
| 2018/0043111 A1* | 2/2018 | Ahern | A61M 15/003 |
| 2018/0369513 A1* | 12/2018 | Hannon | A61M 15/0086 |

FOREIGN PATENT DOCUMENTS

| | | |
|---|---|---|
| EP | 0691865 | 1/1996 |
| RU | 2456026 C2 | 7/2012 |
| WO | WO 2007/144659 A1 | 12/2007 |
| WO | 065707 | 5/2009 |
| WO | WO 2009/065707 A1 | 5/2009 |
| WO | 017358 | 1/2018 |

OTHER PUBLICATIONS

Decision to Grant for RU 202119828 dated Aug. 1, 2023, 16 pgs. Including English translation.
International Search Report and Written Opinion for PCT/IB2020/050232, issued by the European Patent Office, Apr. 9, 2020; 9 pgs.
European Extended Search Report for EP 19151681.4 issued by the European Patent Office; 7 pgs.

* cited by examiner

```
┌─────────────────────────────────┐
│   Store bulk powder in reservoir │ ─ 202        ↙ 200
└─────────────────────────────────┘
              ↓
┌─────────────────────────────────┐
│ Move reservoir towards airway head │ ─ 204
└─────────────────────────────────┘
              ↓
┌─────────────────────────────────┐
│    Selectively limit movement of  │ ─ 206
│   reservoir towards airway head   │
│        to control dosage          │
└─────────────────────────────────┘
              ↓
┌─────────────────────────────────┐
│   Shave portion of bulk powder into │ ─ 208
│    airway of dry powder inhaler   │
└─────────────────────────────────┘
              ↓
┌─────────────────────────────────┐
│     Inhale on dry powder inhaler  │ ─ 210
└─────────────────────────────────┘
              ↓
┌─────────────────────────────────┐
│    Generate a vortical airflow to │ ─ 212
│       aerosolize dry powder       │
└─────────────────────────────────┘
              ↓
┌─────────────────────────────────┐
│   Generate a dampened and/or      │ ─ 214
│   laminar airflow for dry powder  │
│            inhalation             │
└─────────────────────────────────┘
```

FIG. 10

DRY POWDER INHALER DEVICE

This application is the § 371 U.S. National Stage of International Application No. PCT/IB2020/050232, filed 13 Jan. 2020, which claims the benefit of European Application No. 19151681.4, filed 14 Jan. 2019, the disclosures of which are incorporated by reference herein in their entireties.

BACKGROUND OF THE INVENTION

Due to documented health hazards of traditional tobacco cigarettes to smokers and bystanders, there has been a shift in the marketplace to find suitable alternatives for the delivery of nicotine to the lungs of a subject. It may be desirable to deliver a bioactive material to the lungs of a subject. For example, it may be desirable to deliver nicotine to the subject's lungs without the creation of second-hand smoke, and without unpleasant odors associated with traditional tobacco smoking. One mechanism to achieve this is through inhalation of a bioactive material as a dry powder formulation. In such systems, a dry powder inhaler is used to deposit the powder on the inner surfaces of the lungs for absorption into the bloodstream. However, many dry powder inhalers have numerous undesirable features.

For example, many devices are designed for medical conditions where a patient requires immediate or complete delivery of a medicament. These devices deliver the medicament in a single inhalation. Thus, these devices are not suitable for applications that require delivery of dry powder over several inhalations. Further, these devices rely on air currents that flow directly through or across the medicament which causes some of the medicament to travel at high speed and impact undesired portions of the subject's airway.

Other devices rely on overly complicated or awkward mechanisms for their use. For example, propellers have been used to rotate a capsule to expel powder by centrifugal force, or various rotating or sliding mechanisms have been used to deposit discrete amounts of powder into the airflow path of an inhaler. These devices are also difficult to use discretely. Further, many of the prior art designs are for use with capsules or blister packs that contain pre-measured dosage amounts. The mechanisms for switching between dosages is often cumbersome and bulky, since they have to accommodate multiple pre-measured dosages. Further, there is not an easy way to customize the amount of each dosage.

Another existing device is shown in U.S. Pat. No. 6,234,169 to Bulbrook ("Bulbrook"), which describes a cone shaped device that protrudes into a dry powder storage reservoir to generate a vortex-like effect inside the cone. The device uses the vortex to dip down inside the storage reservoir and pick up a slug of powder and deliver it to the airways of an individual. However, a limitation of the Bulbrook design is that it does not provide adequate energy inside the storage reservoir to deagglomerate the powder sufficiently to deliver the desired aerosol to the user. The Bulbrook design also lacks a reliable method of preventing accidental powder release or a feature for switching storage reservoirs. Other designs described in the art, such as European publication No. EP 0691865 to Drought et al., and European publication No. 0407028 to Clark et al., also fail to address many of the deficiencies in the prior art described herein.

It would be desirable to provide a dry powder inhaler can create sufficient turbulence such that increased amounts of powder can be picked up into the airway for user inhalation, while maintaining ease of use in a discrete design. Further, a dry powder inhaler is needed that can dispense a measured yet customizable amount of dry powder for each inhalation. Still further, the inhaler should store the dry powder in a bulk storage reservoir, so that the inhaler does not have to rely on a conventional mechanism that circulates through pre-measured capsules or blister packs.

SUMMARY OF THE INVENTION

In one embodiment, a dry powder inhaler includes an elongate body including a proximal end, a distal end and an air inlet disposed therebetween; a reservoir includes a reservoir cavity; an airway assembly is at least partially housed within the elongate body, the airway assembly includes a first airway; a mouthpiece includes a mouthpiece airway that is connected to the first airway; an airway head is attached to the airway assembly that extends into the reservoir cavity; and at least one airway assembly opening in the airway assembly connects the reservoir cavity to the first airway.

In an embodiment, the airway assembly includes an inner airway element and an outer airway element, the outer airway element at least partially surrounds the inner airway element. In one embodiment, the inner airway element includes an inner element airway, the outer airway element includes an outer element airway, and the inner airway element includes at least one airway passage to connect the inner element airway to the outer element airway. In one embodiment, the outer airway element includes at least one wall opening for connecting the outer element airway to the air inlet. In one embodiment, the inner airway element includes at least one curved fin that protrudes into the outer element airway. In one embodiment, the inner airway element includes a plurality of curved fins that protrude into the outer element airway. In one embodiment, the at least one airway assembly opening is proximal of the airway head. In one embodiment, the at least one airway assembly opening includes a first and second airway assembly opening proximal of the airway head. In one embodiment, the dry powder inhaler includes a reservoir spring positioned distal of the reservoir and configured to bias the reservoir in a proximal direction. In one embodiment, the dry powder inhaler includes a dose selector cam sleeve including a curved groove that is configured to limit movement of the reservoir. In one embodiment, the movement is limited when an element is rotated. In one embodiment, the dry powder inhaler includes a dose selector ring connected to the dose selector cam sleeve that is configured to limit the rotational movement of the dose selector cam sleeve. In one embodiment, the dry powder inhaler includes a chassis including a plurality of indentations to lock the dose selector ring in a plurality of positions. In one embodiment, each of the plurality of positions limits the rotational movement of the dose selector cam sleeve in 45 degree intervals. In one embodiment, the mouthpiece is configured to retract distally into a mouthpiece opening disposed in a proximal end of the body. In one embodiment, the airway assembly includes a plug that at least partially blocks the at least one airway assembly opening when the mouthpiece is fully retracted distally. In one embodiment, the plug unblocks the at least one airway assembly opening when the mouthpiece is fully extended proximally.

The reservoir may be configured to store an amount of dry powder. The reservoir may be configured to store a bulk amount of dry powder. The reservoir may contain an amount of dry powder. The reservoir may contain a bulk amount of dry powder. Storing a bulk amount of dry powder in the reservoir may advantageously allow the inhaler to hold multiple doses of dry powder without the need to store the powder in pre-measured amounts.

The dry powder may comprise a bioactive material. As used herein, the term 'bioactive material' refers to a material which has effect on a living organism, tissue or cell. The bioactive material may comprise a drug. The bioactive material may provide some prophylactic or pharmacologic effect. The bioactive material may comprise at least one physiologically or pharmacologically active substance that produces a localized or systemic effect in a subject.

The bioactive material may comprise at least one of: an antibiotic, an antibody, an antiviral agent, an antiepileptic, an analgesic, an anti-inflammatory agent, and a bronchodilator. The bioactive material may comprise at least on of an inorganic and an organic compound. The bioactive material may be configured to act on at least one of the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system, and the central nervous system.

The bioactive material may comprise at least one of: a polysaccharide, a steroid, a hypnotics or sedative, a psychic energizer, a tranquilizer, an anticonvulsant, a muscle relaxant, an antiparkinson agent, a muscle contractant, an antimicrobial, and an antimalarial. The bioactive material may comprise a hormonal agent. For example, the bioactive material may comprise at least one of a contraceptive, a sympathomimetic, a polypeptide, and a protein capable of eliciting physiological effects, a diuretic, a lipid regulating agent, an antiandrogenic agent, an antiparasitic, a neoplastic, an antineoplastic, and a hypoglycemic. The bioactive material may comprise at least one of a nutritional agent and supplements, a growth supplement, a vitamin or a mineral, an antienteritis agent, an electrolyte, and a diagnostic agent.

The bioactive material may comprise at least one of calcitonin, erythropoietin (EPO), Factor VIII, Factor IX, ceredase, cerezyme, cyclosporine, granulocyte colony stimulating factor (GCSF), alpha-I proteinase inhibitor, elcatonin, granulocyte macrophage colony stimulating factor (GMCSF), growth hormone, human growth hormone (hGH), growth hormone releasing hormone (GHRH), heparin, low molecular weight heparin (LMWH), interferon alpha, interferon beta, interferon gamma, interleukin-2, luteinizing hormone releasing hormone (LHRH), leuprolide, somatostatin, somatostatin analogs including octreotide, vasopressin analog, follicle stimulating hormone (FSH), immunoglobulins, insulin-like growth factor, insulintropin, interleukin-I receptor antagonist, interleukin-3, interleukin-4, interleukin-6, macrophage colony stimulating factor (M-CSF), nerve growth factor, parathyroid hormone (PTH), thymosin alpha I, IIb/IIIa inhibitor, alpha-I antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-I receptor, I3-cis retinoic acid, nicotine, nicotine salt, nicotine bitartrate, nicotine lactate, gentamicin, ciprofloxacin, amphotericin, amikacin, tobramycin, pentamidine isethionate, albuterol sulfate, metaproterenol sulfate, beclomethasone dipropionate, triamcinolone acetamide, budesonide acetonide, ipratropium bromide, flunisolide, fluticasone, fluticasone propionate, salmeterol xinofoate, formeterol fumarate, cromolyn sodium, ergotamine tartrate and analogues, agonists and antagonists of the above.

The dry powder inhaler of the present invention may be configured to deliver a bioactive material to a region of a subject's airway. Pulmonary delivery of a bioactive material may be advantageous as it is relatively non-invasive, may avoid the bioactive material first passing through the metabolism of the subject, may allow direct delivery of the bioactive material to the site of action for the treatment of respiratory diseases, and it may allow the bioactive material to be delivered to a large surface area in the airway of a subject.

The dry powder may comprise a prophylactic or therapeutic agent for the treatment and prevention of pulmonary and systemic disorders. Pulmonary disorders may be difficult to be effectively cured through conventional modes of dosage system. The pulmonary and systemic disorders include chronic obstructive pulmonary disease, lung cancer, cystic fibrosis, tuberculosis, and asthma.

The prophylactic or therapeutic agent for the treatment and prevention of pulmonary and systemic disorders may comprise at least one of: a β2 adrenergic agonist, a corticosteroid and a cromone, and an anticholinergic. Corticosteroid inhalers (dry-powder or metered-dose inhalers) have become the primary anti-inflammatory treatment for adults and are very widely used in children. Systemically active corticosteroids (e.g. prednisone or dexamethasone) can be inhaled.

The dry powder may comprise at least one of a peptide or a protein. Direct administration to the lungs for local action allows high doses of protein and peptides to be distributed while preventing systemic adverse effects. For example, the dry powder may comprise at least one of insulin, human growth hormone (hGH), calcitonin, and parathyroid. These may be used to treat diabetes, hormone deficiency, and osteoporosis, respectively. Other examples include but are not limited to recombinant human granulocyte colony stimulating factor to treat bone disorders.

The dry powder may comprise at least one antibiotic. For example, the dry powder may comprise tobramycin as maintenance therapy for cystic fibrosis (CF) patients with chronic Pseudomonas aeruginosa infection.

The dry powder may comprise at least one vaccine. The vaccine may be a prophylactic or a therapeutic vaccine. For example, the dry powder may comprise inulin-stabilized influenza subunit vaccine prepared by spray-freeze drying to induce systemic, mucosal humoral as well as cell-mediated immune responses.

The dry powder may comprise nicotine. As used herein, the term "nicotine" refers to nicotine and nicotine derivatives in any form, including but not limited to, a free-base nicotine, nicotine salt, or in a matrix such as a sugar matrix or organometallic complex.

In one embodiment, a method for dispensing dry powder into an airway of a dry powder inhaler includes the steps of storing a bulk amount of dry powder in a reservoir; and shaving a portion of the bulk dry powder into an inhalation airway of the dry powder inhaler. In one embodiment, the method includes moving the reservoir towards an airway head during the step of shaving. In one embodiment, the method includes limiting the movement of the reservoir during the step of shaving to one of a plurality of selectable positions. In one embodiment, a method of inhaling dry powder from a dry powder inhaler includes the steps of dispensing the dry powder into an airway of the dry powder inhaler; inhaling on the dry powder inhaler to generate a negative pressure within the airway to aerosolize and inhale the dry powder. In one embodiment, the step of inhaling includes generating a vortical (or vortex) airflow within the airway to aerosolize the dry powder. In one embodiment, the step of inhaling includes dampening the vorticial (or vortex) airflow within the airway to inhale the dry powder.

In one embodiment, a dry powder inhaler includes a first airway including at least one protrusion configured to generate a vorticial (or vortex) airflow; and a second airway connected to the first airway by a transition airway configured to dampen the vorticial (or vortex) airflow.

In one embodiment, a method for dry powder inhalation includes the steps of storing a bulk amount of dry powder in a reservoir; moving a portion of the bulk dry powder into first airway of the dry powder inhaler; generating a vorticial (or vortex) airflow in the first airway to aerosolize the portion of the bulk dry powder; and dampening the vorticial (or vortex) airflow in a transition airway connected to the first airway.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 10 is a flow chart of a method for dispensing dry powder into an airway of a dry powder inhaler according to one embodiment.

DETAILED DESCRIPTION OF THE INVENTION

Figure 1A:
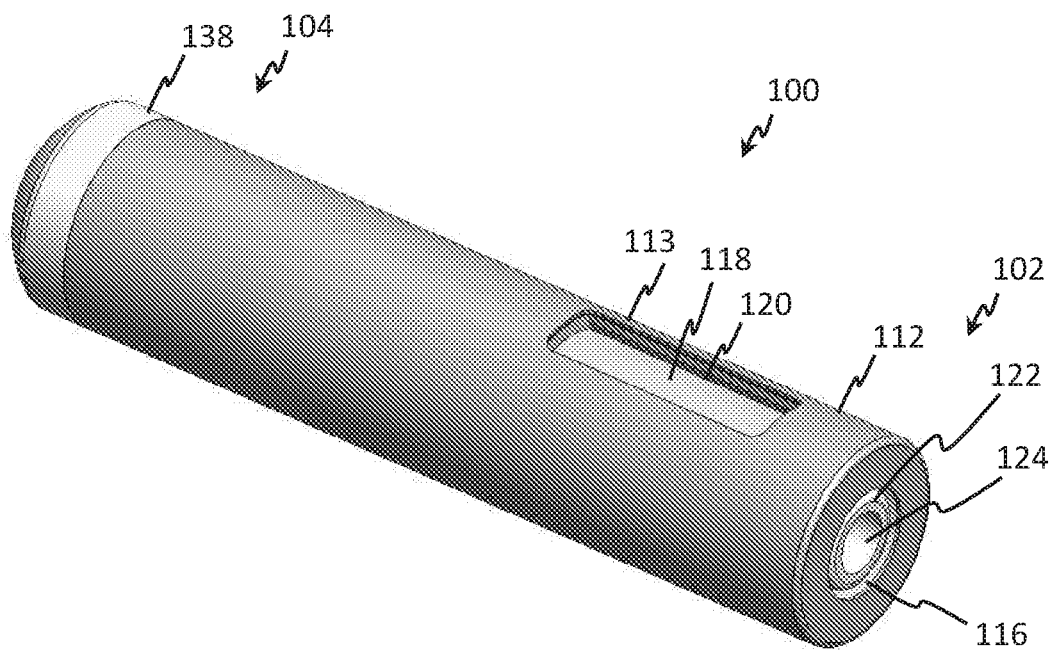
FIG. 1A is a perspective view of a dry powder inhaler with the mouthpiece retracted according to one embodiment.

It is to be understood that the figures and descriptions of the present invention have been simplified to illustrate elements that are relevant for a more clear comprehension of the present invention, while eliminating, for the purpose of clarity, many other elements found in dry powder inhalation devices, systems and methods. Those of ordinary skill in the art may recognize that other elements or steps are desirable or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (that is, to at least one) of the grammatical object of the article. By way of example, "an element" means one element or more than one element.

Referring now in detail to the drawings, in which like reference numerals indicate like parts or elements throughout the several views, in various embodiments, presented herein is a dry powder device and method.

Figure 1B:
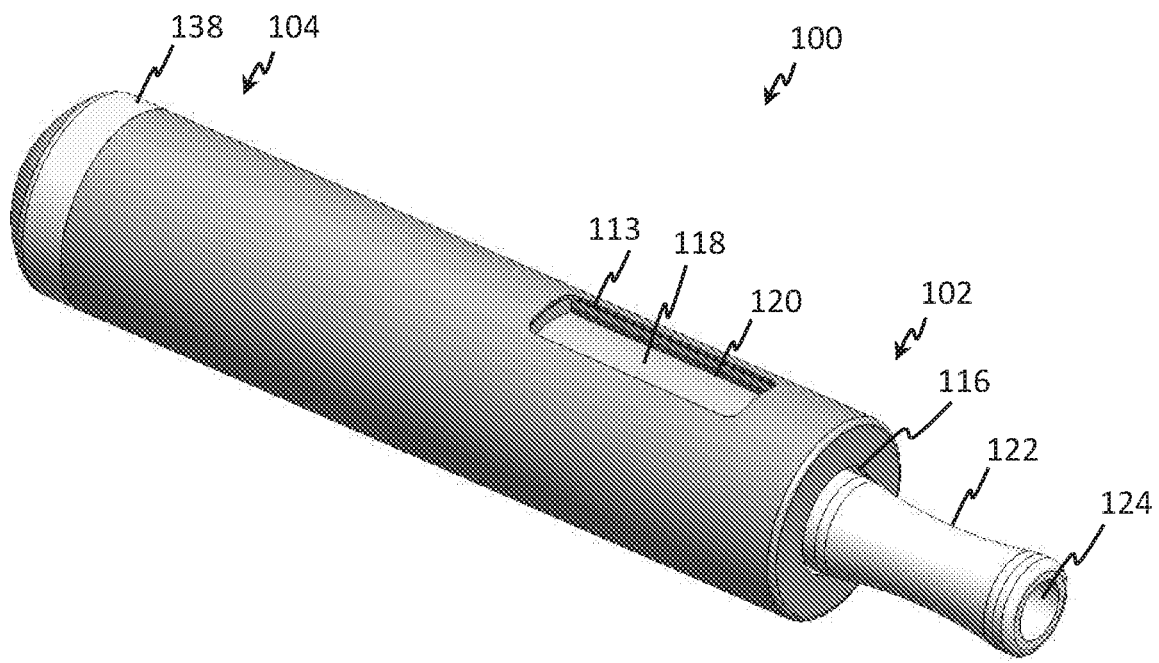
FIG. 1B is a perspective view of a dry powder inhaler with the mouthpiece extended according to one embodiment.
Figure 1C:
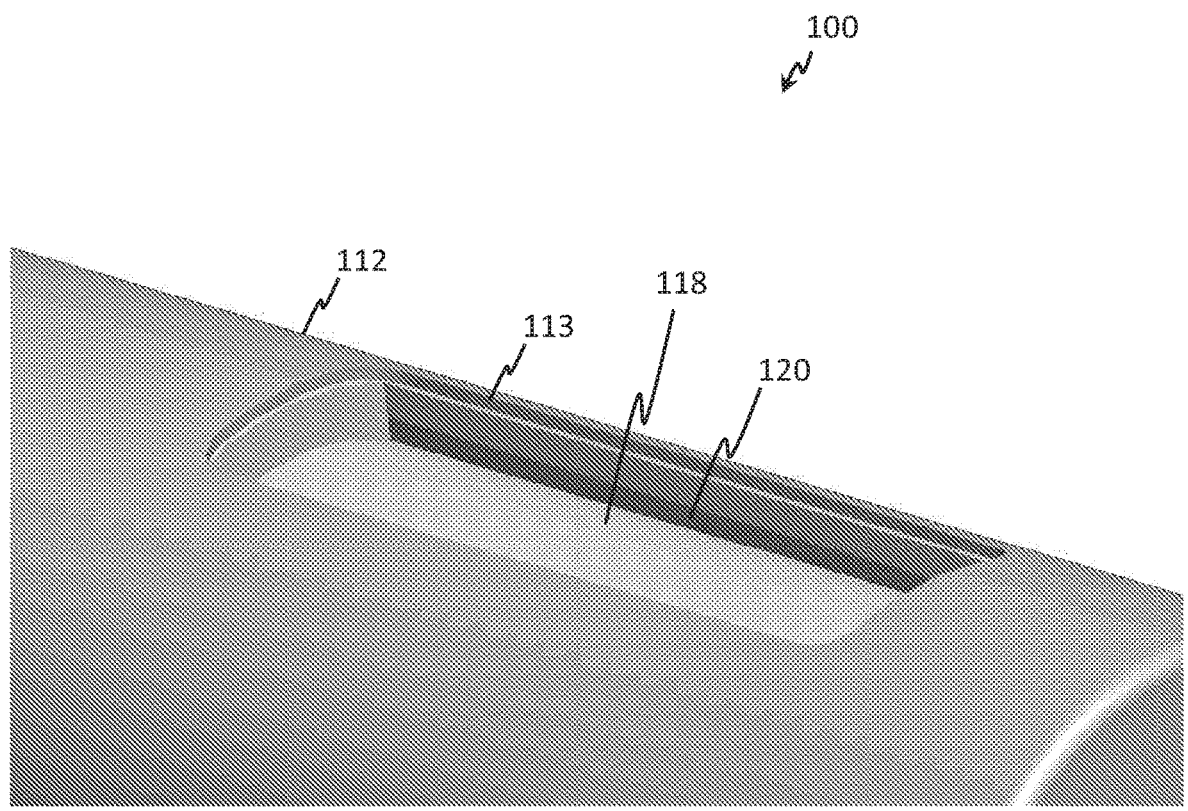
FIG. 1C is a magnified view of an external air inlet according to one embodiment.

A fully assembled dry powder inhaler 100 is shown in FIGS. 1A and 1B according to one embodiment. The dry powder inhaler 100 has an elongate body cover 112 which has an air inlet opening 113 for accommodating air inlets 120 in the chassis 118. One of the air inlets 120 is shown in more detail in the magnified view of FIG. 10. A second air inlet (not shown) in the chassis 118 runs opposite and parallel to the air inlet 120, also positioned within the opening 113. With reference back to FIGS. 1A and 1B, a mouthpiece opening 116 is disposed in the proximal end 102 of the inhaler 100, and is sized to allow a retractable mouthpiece 122 to deploy and extend through it. The mouthpiece 122 has a mouthpiece lumen 124 that connects to airways of the inhaler 100 for generating a negative vorticial (or vortex) airflow and aerosolizing powder in airways of the device. A dose selector ring 138 extends from the distal end 104 of the inhaler 100, abutting the distal end of the body cover 112.

The body cover in one embodiment is generally cylindrical, however, the profile of the body cover can be any shape, such as square, pentagonal, hexagonal, or otherwise have any number of flat or curved sides. In one embodiment, the body cover is interchangeable, so that users can swap body covers to give the device a different visual look at any time. Skins can also be used to slip over a body cover to quickly change the look of the inhaler. In one embodiment, the surface of the body cover may be contoured as desired so that the inhaler is easier to hold. The body cover can also have one or more textured gripper portions.

Figure 2:
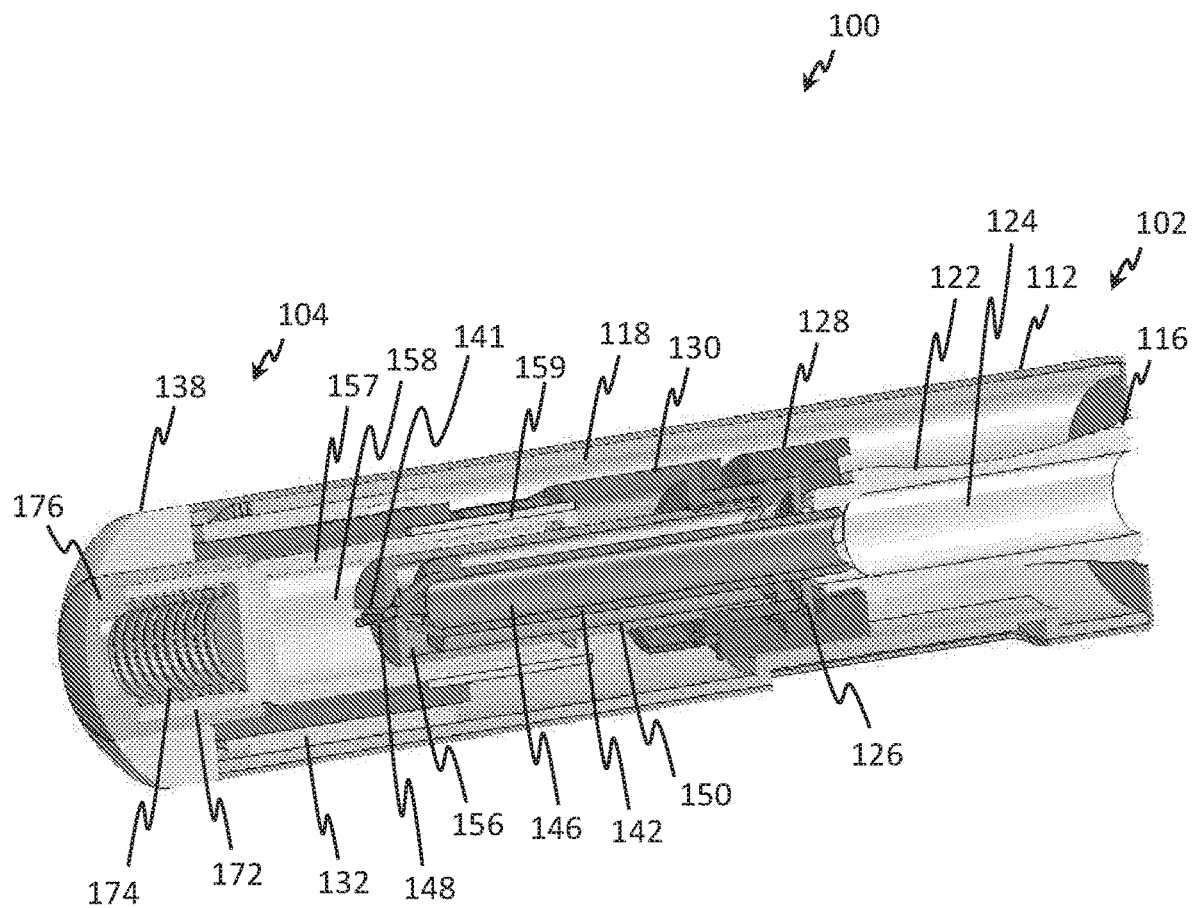
FIG. 2 is a perspective cross-sectional view of a dry powder inhaler according to one embodiment.

A cross-sectional view of a dry powder inhaler 100 is shown in FIG. 2, according to one embodiment. The mouthpiece 122 is shown in a retracted position, so that it remains inside the mouthpiece opening 116. When the mouthpiece 122 is pulled out proximally 102, an inner airway element 142 attached to the mouthpiece 122 also slides in a proximal direction 102. The mouthpiece 122 has a mouthpiece lumen 124 that is connected to the airway 146 of the inner airway element 142. The mouthpiece 122 is connected inline to a slider 128 and a reservoir driver 130. The inner airway element 142 is coaxially surrounded by an outer airway element 150. The distal ends of the inner and outer airway elements 142, 150 extend into the reservoir cavity 158, where bulk amounts of dry powder can be stored.

The reservoir 157 is secured into place by a reservoir cap 159. The inner airway element 142, outer airway element 150, reservoir 157 and reservoir cap 159 are at least partially surrounded by the reservoir driver 130. At the distal end 104 of the device 100, a dose selector ring 138 is operably connected to a dose selector cam sleeve 132 for controlling the amount of dry powder that is distributed into the airway before an inhalation. A reservoir spring button 176 at the distal end of the device 100 at least partially houses a reservoir spring 174 which pushes on a reservoir spring piston 172. The reservoir spring button 176 can be depressed to eject the reservoir 157 as explained in further detail below. The inner and outer airway elements 142, 150 are configured so that when the mouthpiece 122 and inner airway element 142 are pushed in distally, the inner airway element plug 148 blocks and seals the distal tip opening in the outer airway element 150. This helps to keep the bulk stored powder sealed for freshness when the device 100 is not in use, since bulk powder exposed to external elements such as humid air may tend to clump the powder.

When the mouthpiece 122 and inner airway element 142 are pulled out, the distal tip opening in the outer airway element 150 is unplugged, and as the reservoir 157 pushes and spins towards the sharp or beveled edge of the airway head 141, an amount of dry powder packed within the reservoir cavity 158 is shaved off by the airway head 141 and deposited into airways 156, 146 of the inner and outer airway elements 142, 150. This action and configuration of the reservoir 157 and the inner and outer airway elements 142, 150 will be explained in further detail below, with reference to the magnified views and embodiments of FIGS. 3A-3G.

Figure 3A:
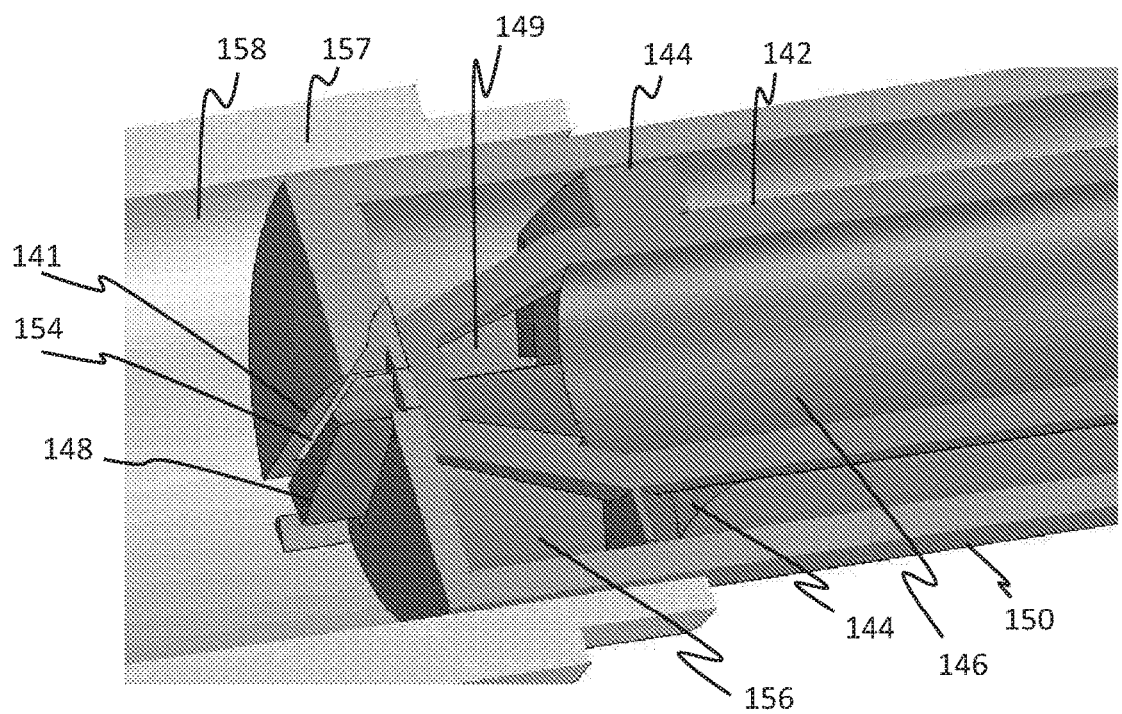
FIG. 3A is a magnified cross-sectional view of an airway assembly according to one embodiment.
Figure 3B:
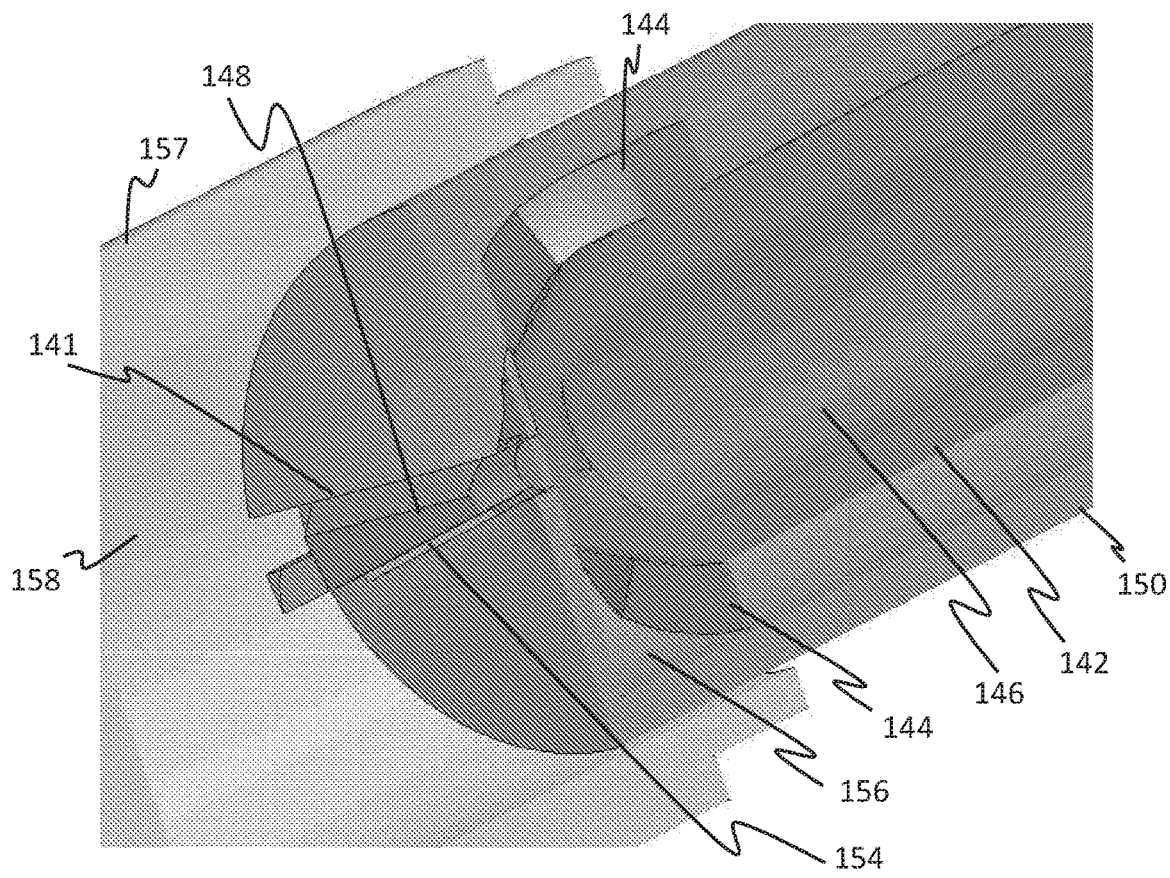
FIG. 3B is an alternate magnified cross-sectional view of an airway assembly according to one embodiment.

With reference to FIG. 3A, according to one embodiment, the outer airway element 150 has an airway head 141 with a sharp or beveled tip, or a tip that is otherwise designed to shave off, scrape or move portions of the bulk powder stored in the reservoir cavity 158 through the opening 154. An inner airway element plug 148 extends through an opening 154 of the outer airway element 150 and into the reservoir cavity 158. Advantageously, the plug 148 blocks external air from circulating into the reservoir cavity 158 when the inner airway element 142 is pushed in while the device 100 is not in use. The plug 148 also blocks exposure of the bulk powder in the reservoir cavity 158 to the airway head 141, preventing the bulk powder from being disturbed or segmented by the airway head 141 while the device 100 is not in use.

Figure 3C:
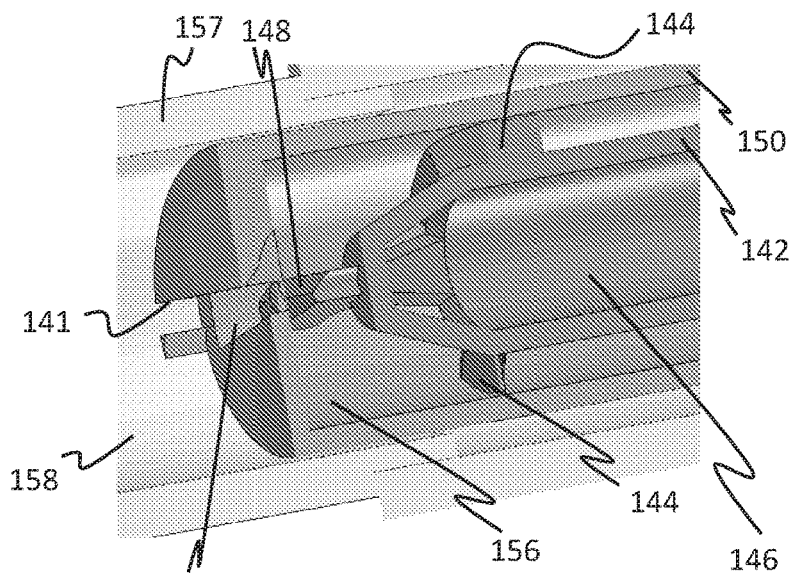
FIGS. 3C-3E are magnified views of an airway assembly with the inner airway element (and mouthpiece) pulled out according to one embodiment.
Figure 3D:
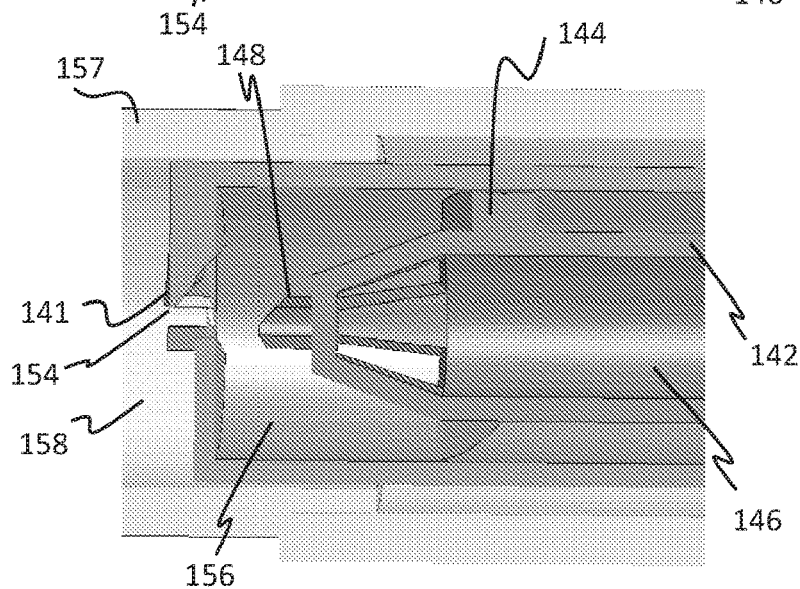
Figure 3E:
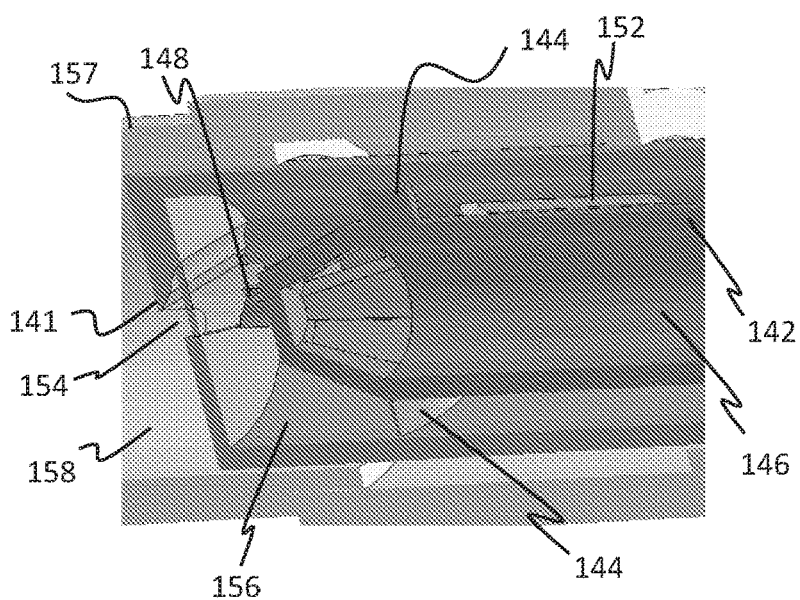

Alternate views of the inner and outer airway element 142, 150 while the inner airway element 142 (and mouthpiece) are pulled out proximally are shown in FIGS. 3C-3E. When the inner airway element 142 is pulled out proximally, the airway head 141 and opening 154 are exposed. The airway head 141 can have one or more edges that can shave off portions of dry powder as the airway head 141 comes into contact with compacted dry powder stored in the reservoir cavity 158. Thus, as the reservoir 157 and reservoir cavity 158 moves towards the airway head 141 and rotates, portions of dry powder stored in the reservoir cavity 158 will shave off the bulk stored powder and fall through the opening 154. Most of the shaved dry powder will fall into the outer element airway 156, while some could fall into the inner element airway 146. Fins 144 on the inner airway element 142 are curved to facilitate the generation of a vortical (or vortex) airflow through the outer element airway 156, which will be described in greater detail below with reference to FIGS. 4A and 4B.

With reference still to FIGS. 3A-3E, the airway head 141 can be adjacent to the opening 154, or there can be openings 154 on either side of the airway head 148.

Figure 3F:
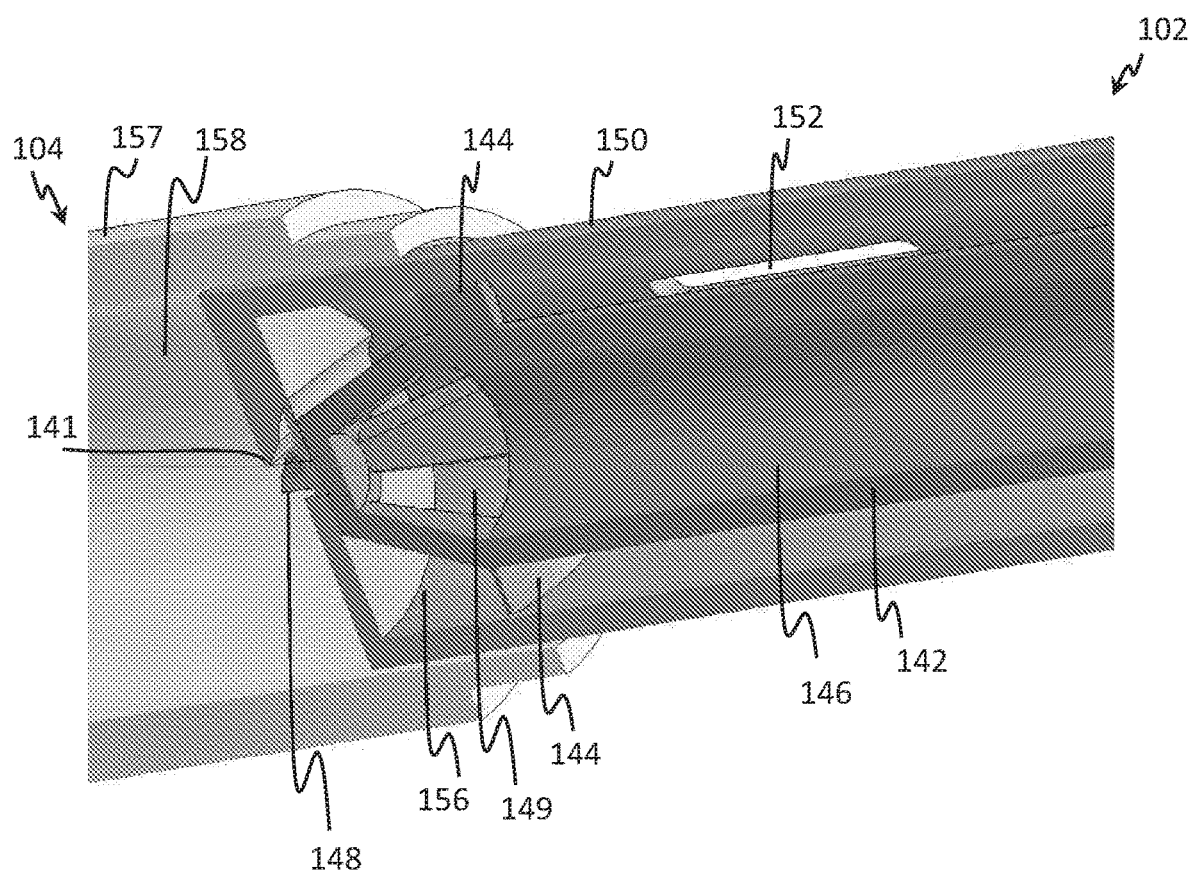
FIG. 3F is an alternate magnified cross-sectional view of an airway assembly according to one embodiment.
Figure 3G:
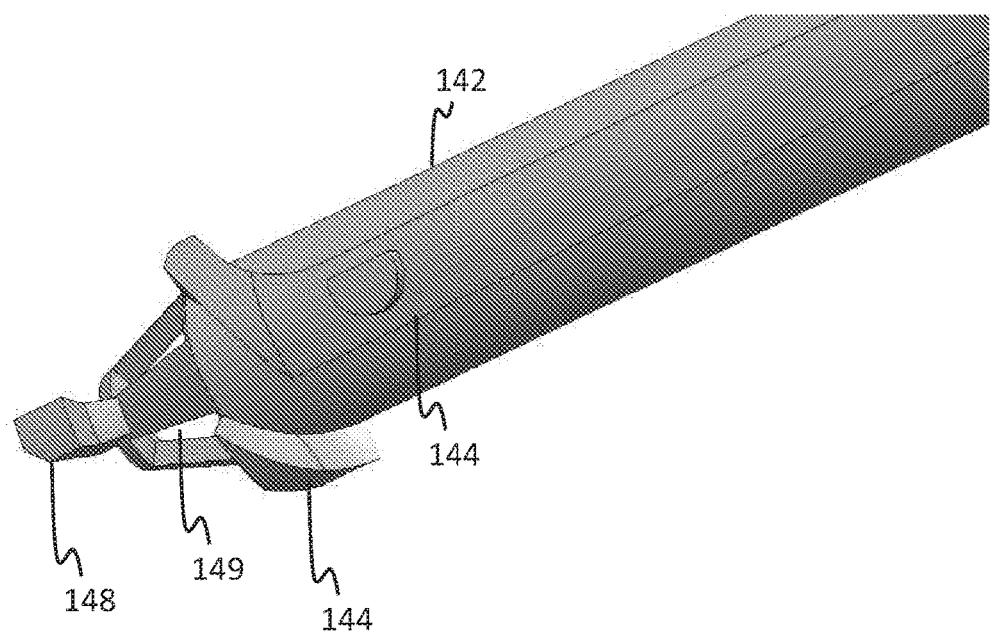
FIG. 3G is a magnified perspective view of an inner airway element according to one embodiment.

As viewed from another angle in FIG. 3F, the distal end 104 of the inner airway element 142 has a number of slots 149 serving as a transition airway to connect the inner element airway 146 with the outer element airway 156. An outer airway element slot 152 is in airflow communication with the air inlet 120, or otherwise in airflow communication with external or ambient air for drawing air into the outer element airway 156 when a negative pressure is applied to the mouthpiece lumen 124. An isolated inner airway element is shown in FIG. 3G from an alternative angle, showing the curvature of the fins 144 for facilitating and generating a vortical (or vortex) flow through airways of the device 100.

Figure 4A:
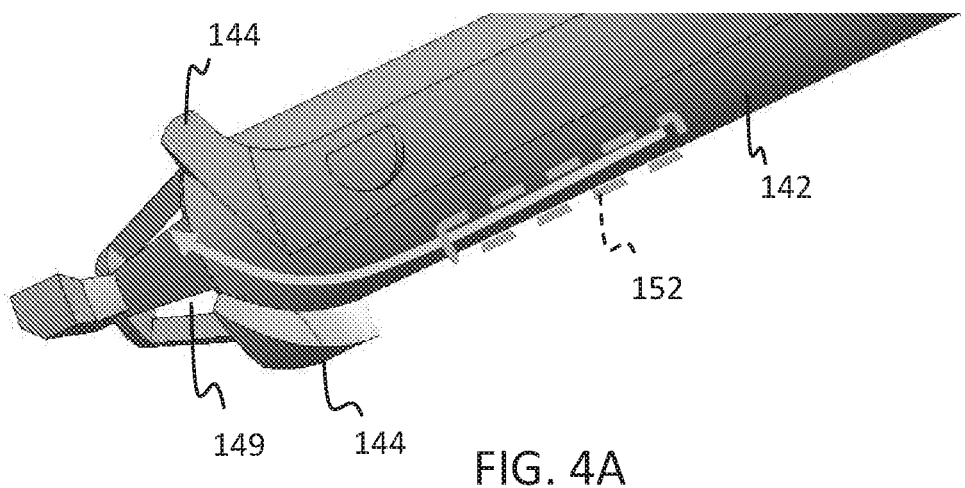
FIG. 4A is a magnified perspective view of an inner airway element according to one embodiment, with an inhalation airflow pathway shown.
Figure 4B:
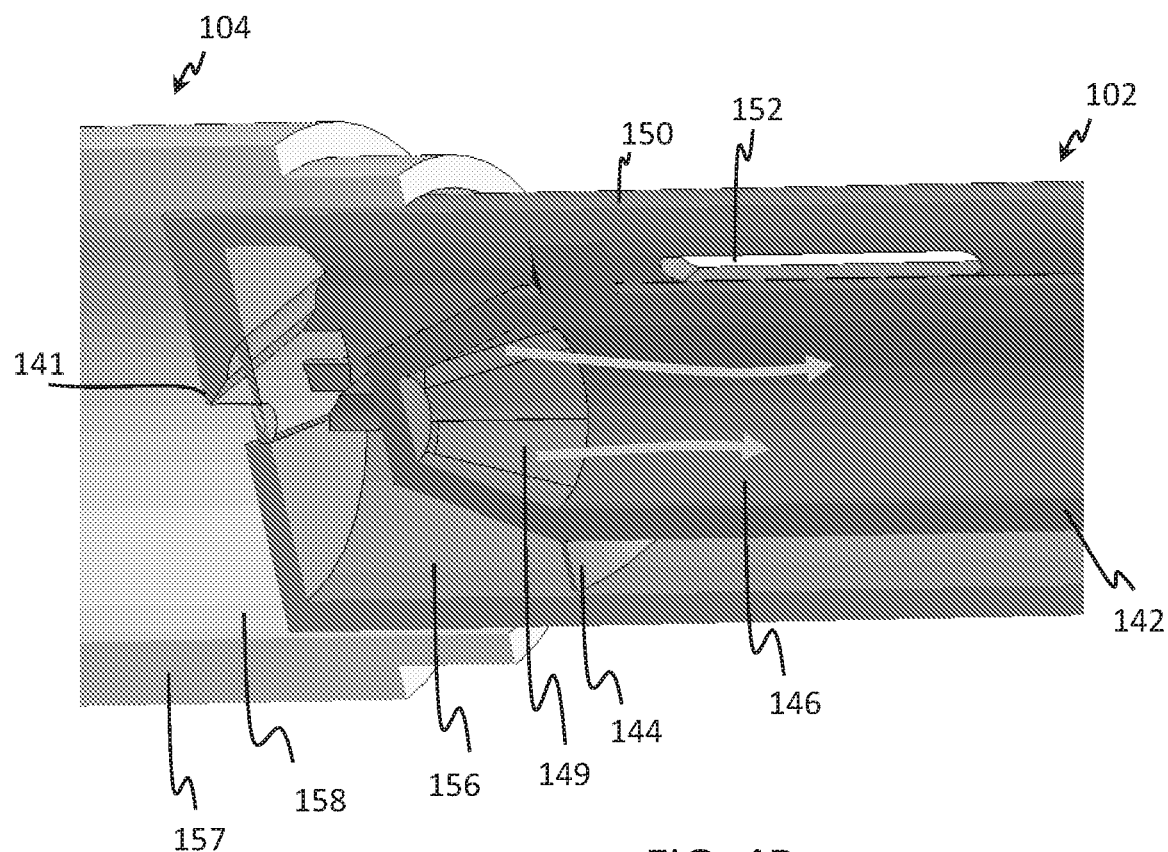
FIG. 4B is a magnified cross-sectional view of airway assembly according to one embodiment, with an inhalation airflow pathway shown.

A depiction of airflow dynamics through the inner and outer element airways 146, 156 is shown now with reference to FIGS. 4A-4B, according to one embodiment. FIG. 4A shows the inner airway element 142 in isolation, with a representation of the outer airway element slot position 152. FIG. 4B shows the inner airway element 142 pulled back proximally, and the outer airway element 150 inserted into the reservoir 157.

Arrows in FIGS. 4A and 4B represent the general direction of airflow. The system generates a two-stage air movement of vortical or vorticial (that is, vortex) airflow for lifting dosages of powder deposited in the outer element airway 156 followed by dampened and laminar airflow within the inner element airway 146. The arrow in FIG. 4A shows stage one airflow through the outer element airway 156 as it approaches the inner airway element slots 149. The air is drawn from an external or ambient air source through the outer airway element slot 152. Since the air is directed through the curved fins 144, a vorticial (that is, vortex) airflow is generated.

The device is primed prior to a user inhalation, so that a desired portion of dry powder is shaved off and present within the outer and inner element airways 156, 146. Prior to and as the vorticial (that is, vortex) airflow enters the slots 149, it aerosolizes the dosage of dry powder that was dispensed into the airway. The slots 149 initiate the transition to stage two airflow. The slots 149 have a geometry that will dampen the vorticial (that is, vortex) airflow and convert the vorticial (that is, vortex) airflow to a more laminar airflow. The dampened laminar airflow continues proximally towards the mouthpiece lumen, efficiently and effectively carrying the aerosolized powder into the user's mouth and lungs at a comfortable flow and pressure level. Advantageously, the two-stage air movement maximizes both powder aerosolization and user comfort.

Figure 5A:
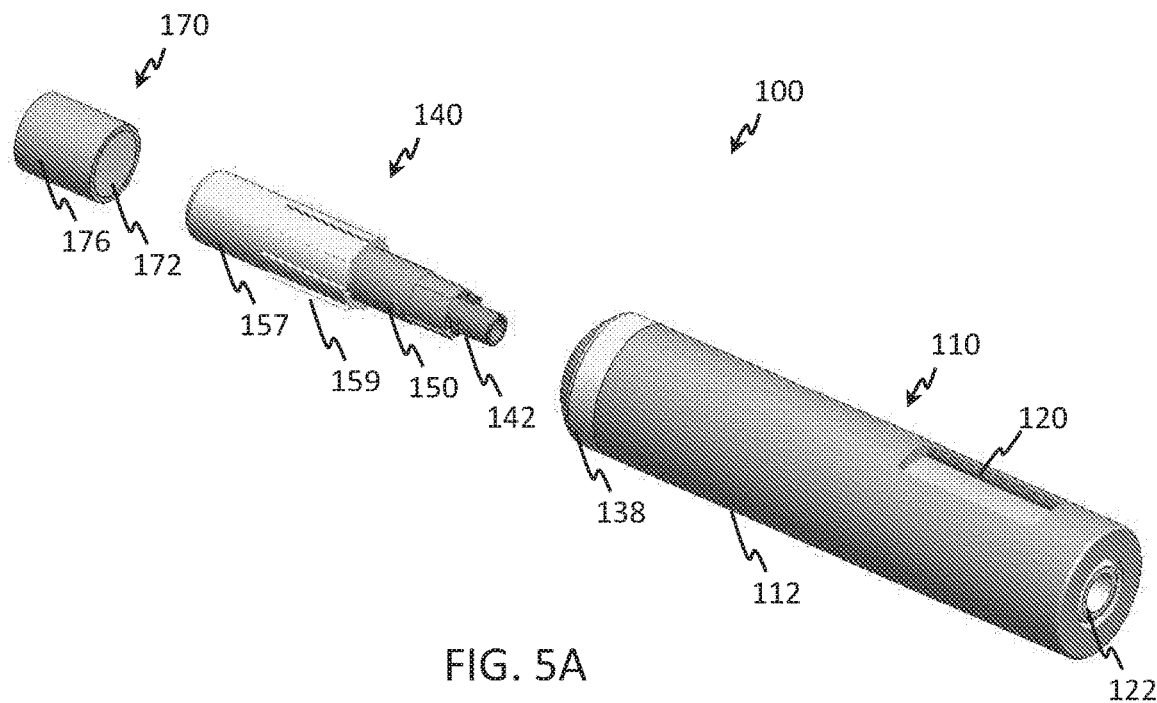
FIG. 5A is a perspective exploded view of three assemblies of a dry powder inhaler according to one embodiment. The spring assembly 170, airway assembly 140 and driver assembly 110 are shown.
Figure 5B:
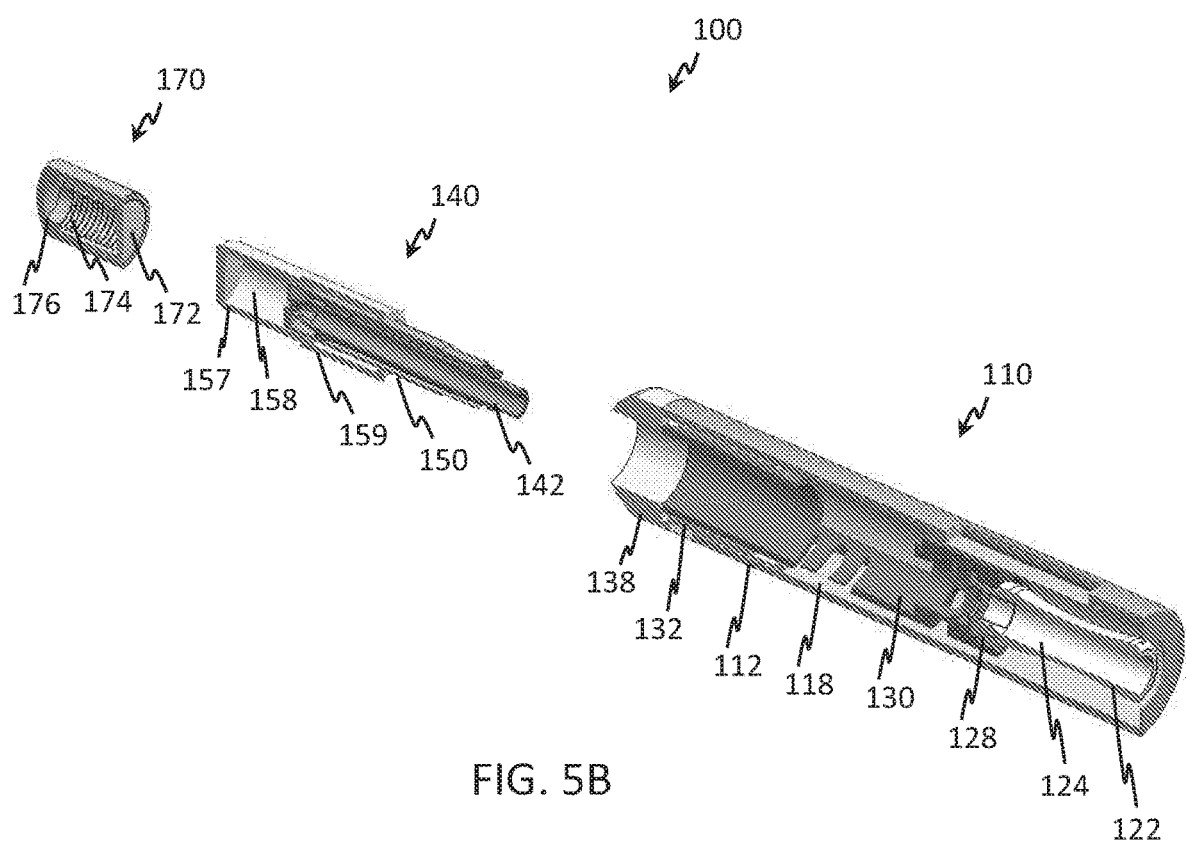
FIG. 5B is a perspective exploded cross-sectional view of the assemblies of a dry powder inhaler shown in FIG. 5A.

With reference now to FIGS. 5A and 5B, the three primary assemblies of the dry powder inhaler 100 are shown in exploded views. The driver assembly 110 includes the body 112 or elongate body 112 coaxially surrounding the chassis 118. Inside the chassis 118 is the mouthpiece 122, which is connected in-line with the slider 128 and the reservoir driver 130. The dose selector ring 138 is attached to the dose selector cam sleeve 132 at the distal tip of the assembly 110.

Figure 6A:
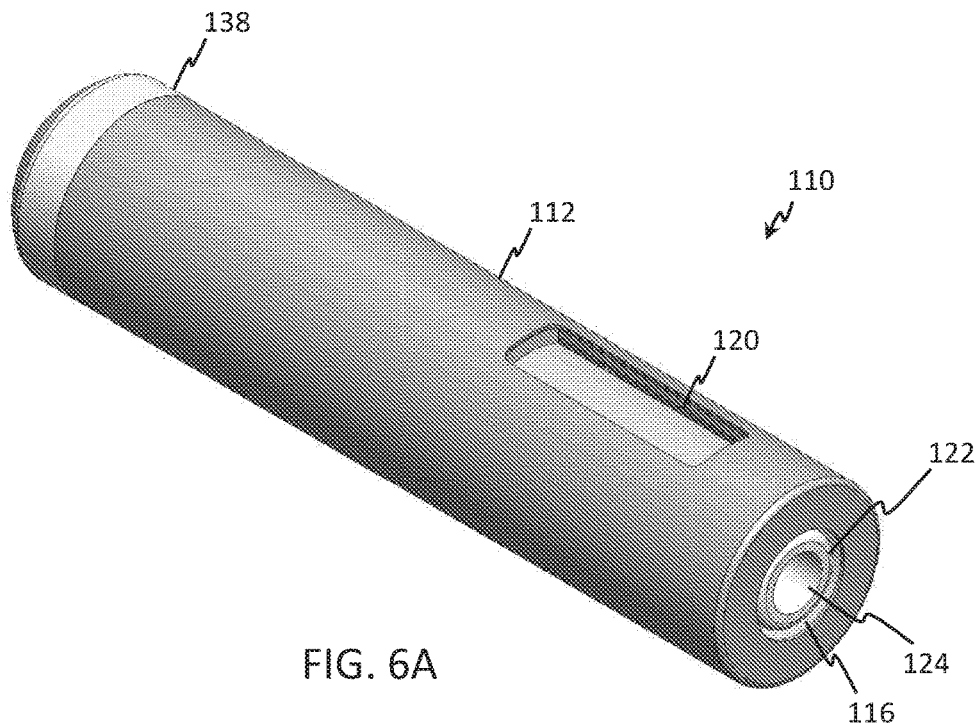
FIG. 6A is a perspective view of a driver assembly according to one embodiment.
Figure 6B:
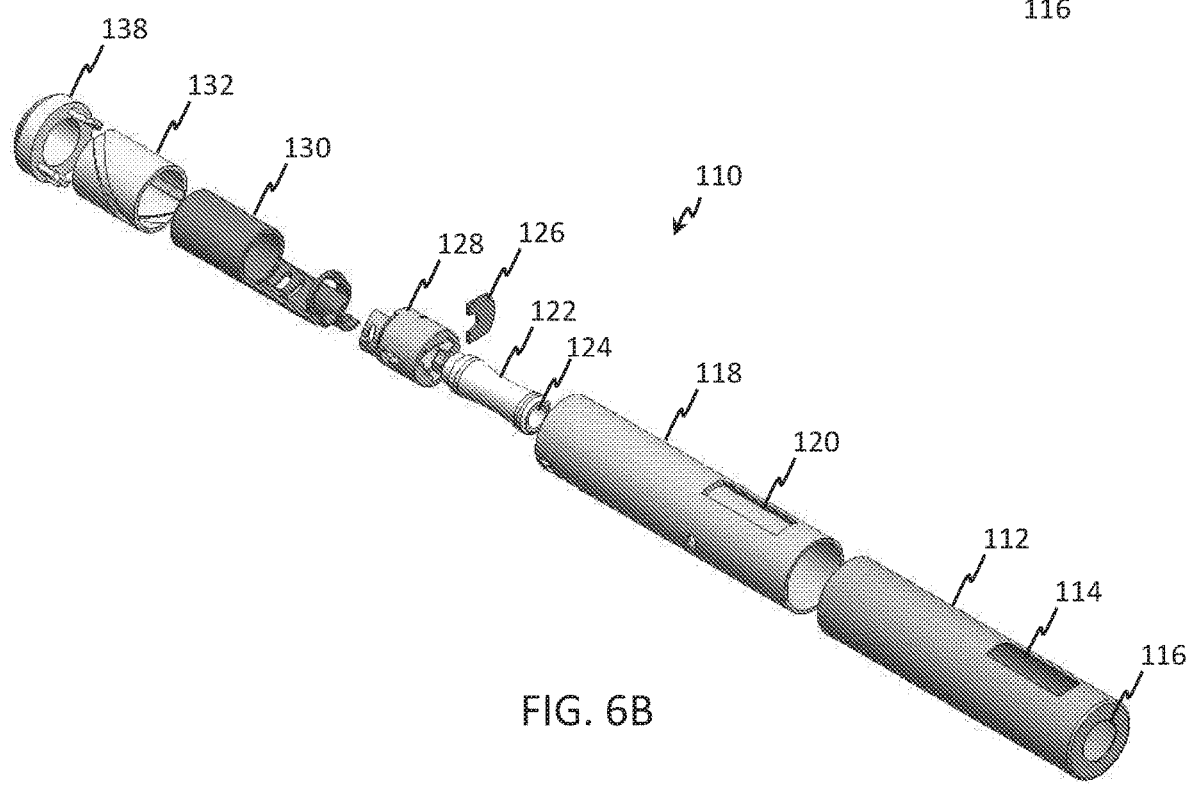
FIG. 6B is a perspective exploded view of a driver assembly according to one embodiment.
Figure 7A:
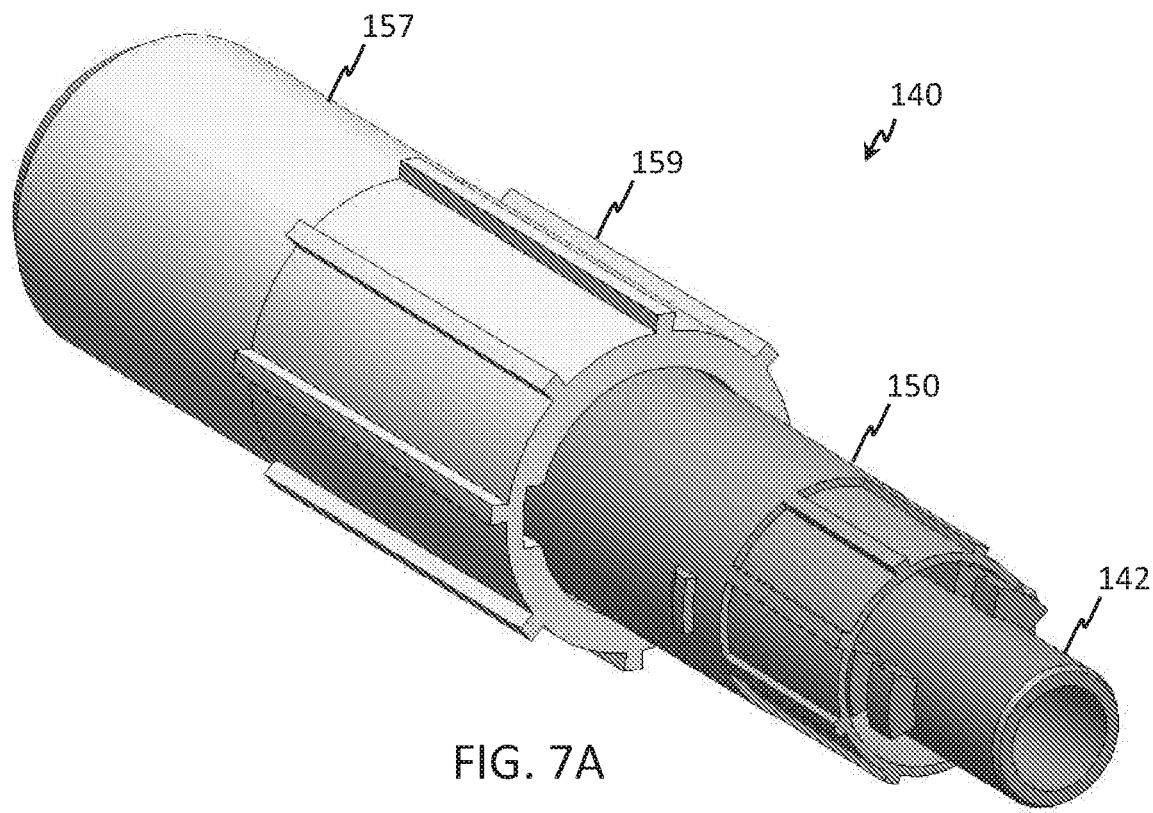
FIG. 7A is a perspective view of an airway assembly according to one embodiment.
Figure 7B:
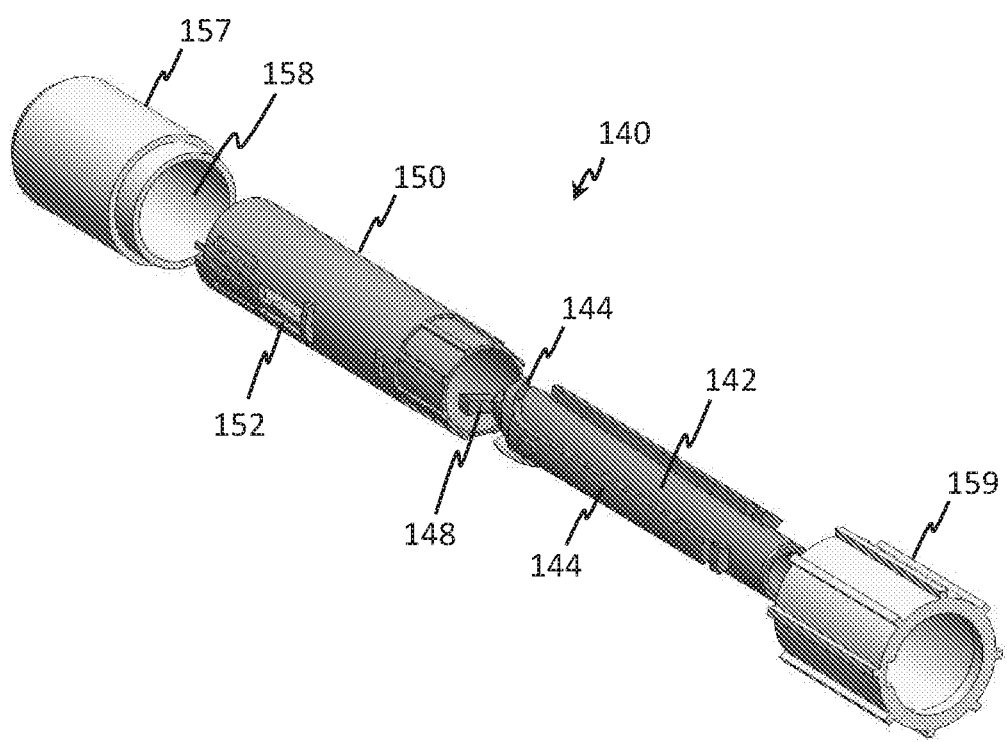
FIG. 7B is a perspective exploded view of an airway assembly according to one embodiment.
Figure 7C:
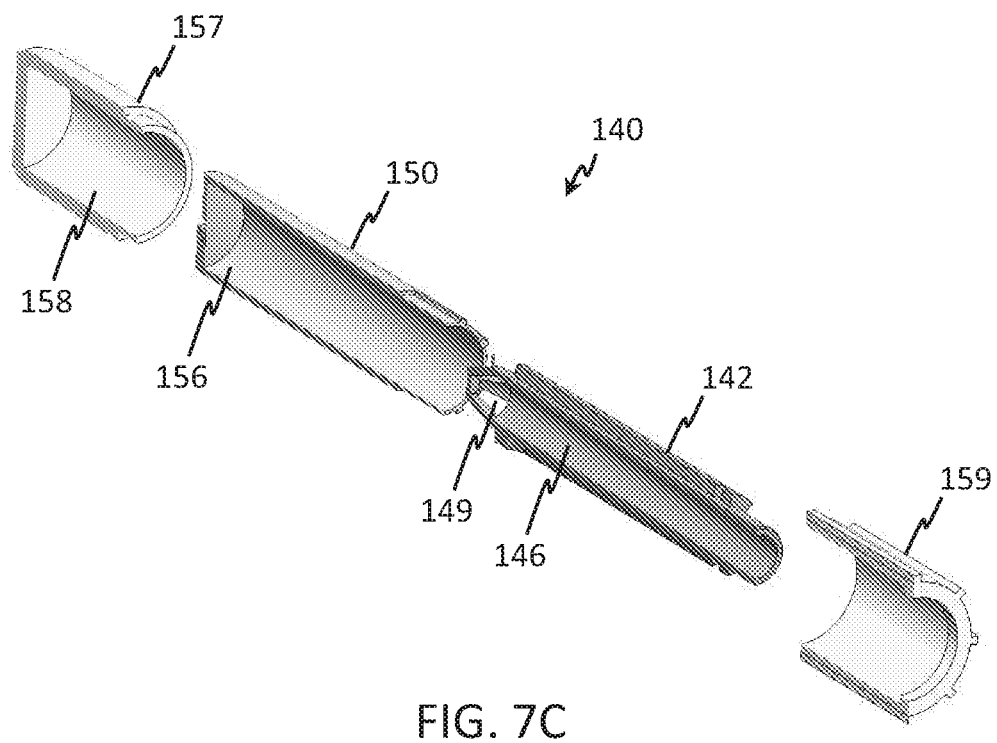
FIG. 7C is a perspective exploded cross-sectional view of an airway assembly according to one embodiment.
Figure 7D:
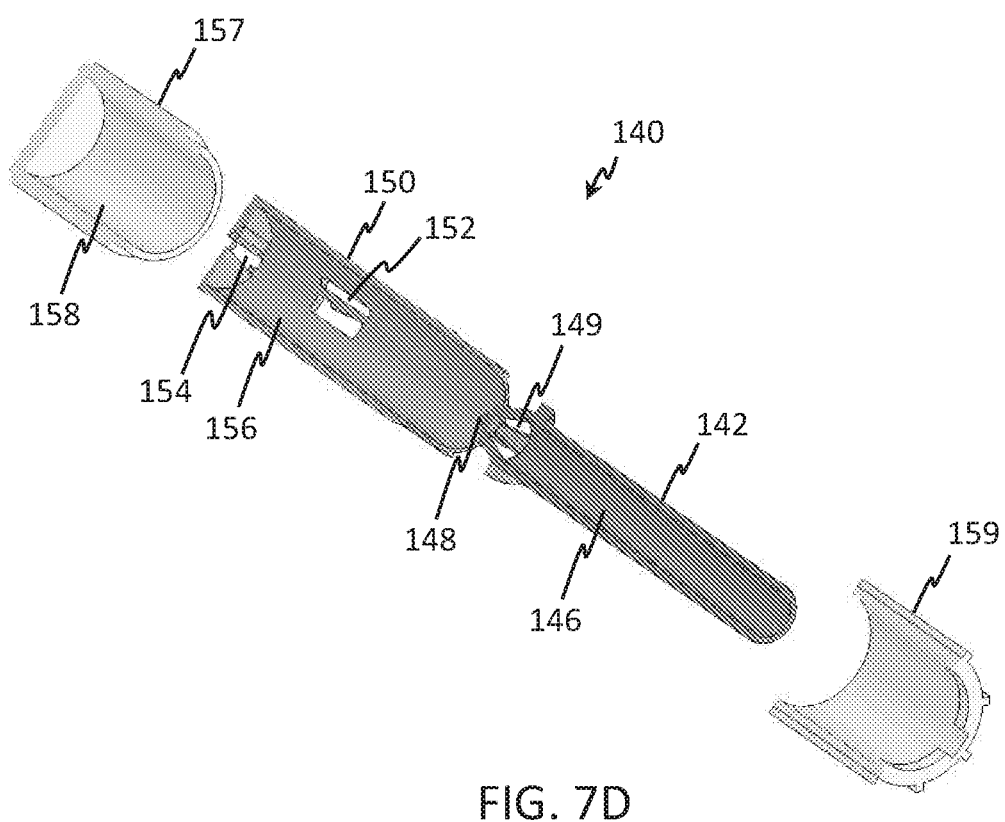
FIG. 7D is an alternate perspective exploded cross-sectional view of the airway assembly shown in FIG. 7C.

With specific reference now to the driver assembly 110 as shown in FIGS. 6A and 6B, air inlets 120 in the chassis 118 are positioned to allow external air into airways of the device during inhalation for generating a vorticial (that is, vortex) airflow. An airway lock 126 can slide in and out to block the airway connection between the mouthpiece lumen and the inner airway element 142. The dose selector ring 138 can be rotated to set the dose selector cam sleeve 132 for controlling how much dry powder is deposited into airways of the device for each inhalation. This process is described in detail with reference to FIGS. 9A-9D.

With reference back to FIGS. 5A and 5B, the airway assembly 140 includes the outer airway element 150 coaxially surrounding part of the inner airway element 142. The reservoir 157 is secured to the distal end of the outer airway element 150 by the reservoir cap 159. To reload the reservoir with more powder, the airway assembly 140 can be easily removed by depressing the button on the spring assembly 170 to eject the spring assembly 170, allowing the airway assembly 140 to easily slide out for refill or disposal and replacement. The reservoir cap 159 can be easily replaced and the airway and spring assemblies 140, 170 reinserted for subsequent use. New airway assemblies 140 with prepacked bulk dry powder can also be swapped in and out of the device (e.g. for the user to experience different flavors or types of powders on the same device).

With specific reference now to the airway assembly 140 as shown in FIGS. 7A-7D, assembled (FIG. 7A) and exploded views (FIGS. 7B-7D) are shown. As explained in part above, the airway plug 148 extends through an opening 154 of the outer airway element 150 and into the reservoir cavity 158. When the inner airway element 142 is pulled back distally and as the reservoir 157 moves towards the airway head 141 and rotates, portions of the stored dry powder in the reservoir cavity 158 will push through the opening 154 so that is can be picked up by the vorticial (that is, vortex) airflow. Fins 144 on the inner airway element 142 are curved to facilitate the generation of a vorticial (that is, vortex) airflow. Slots 149 connect the inner element airway 146 with the outer element airway 156. An outer airway element slot 152 connects the outer element airway 156 to external or ambient air.

Figure 8A:
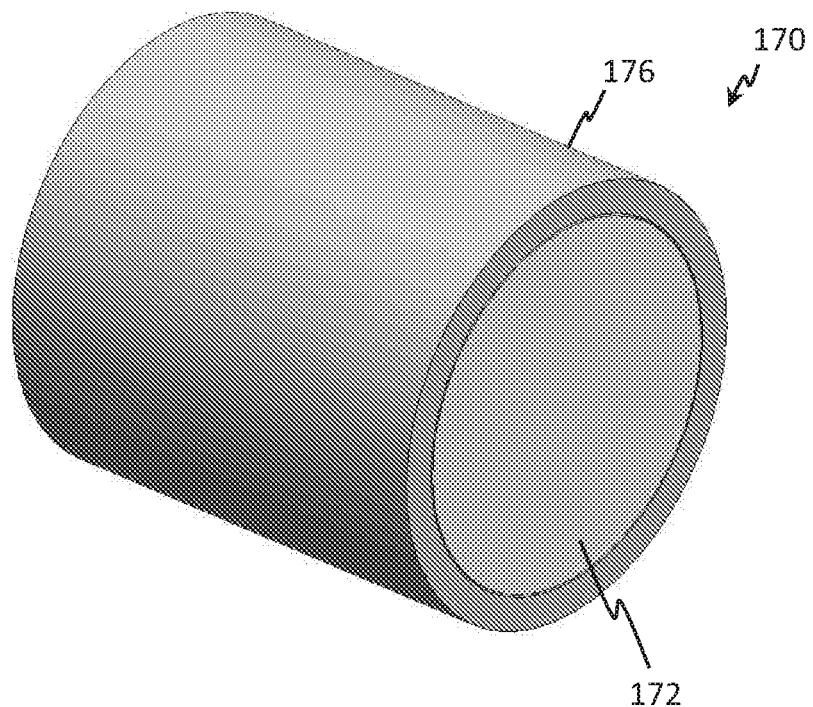
FIG. 8A is a perspective view of a spring assembly according to one embodiment.
Figure 8B:
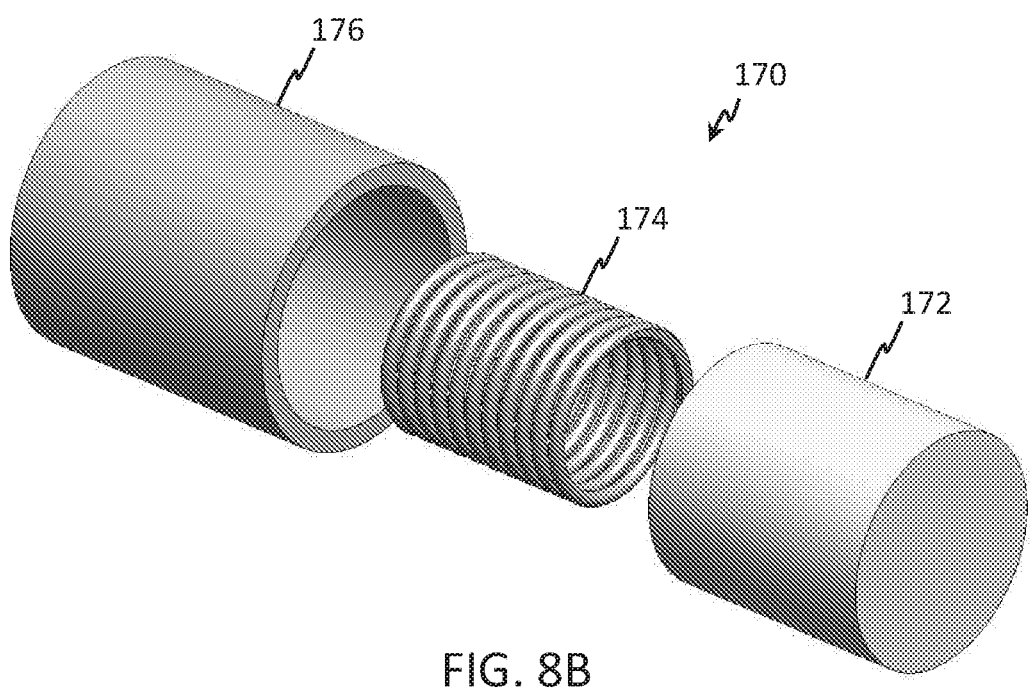
FIG. 8B is a perspective exploded view of a spring assembly according to one embodiment.
Figure 9A:
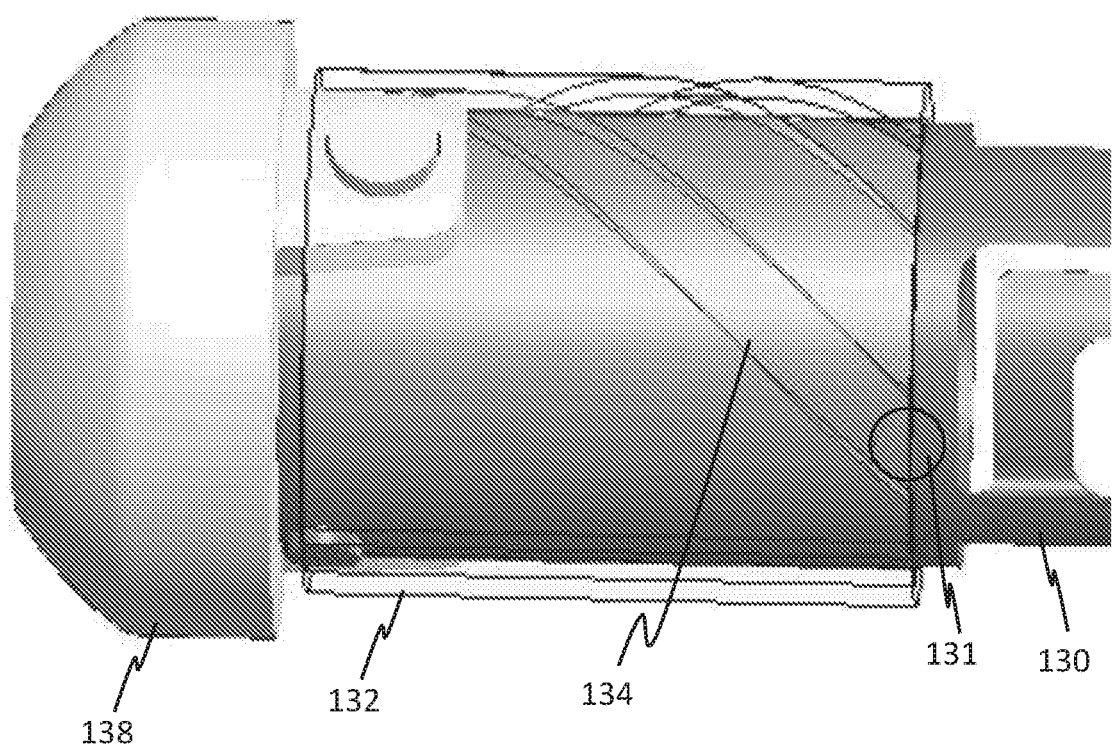
FIG. 9A is a magnified side view of a partially assembled driver assembly (the dose selector cam sleeve is transparent for illustrative purposes) according to one embodiment.
Figure 9B:
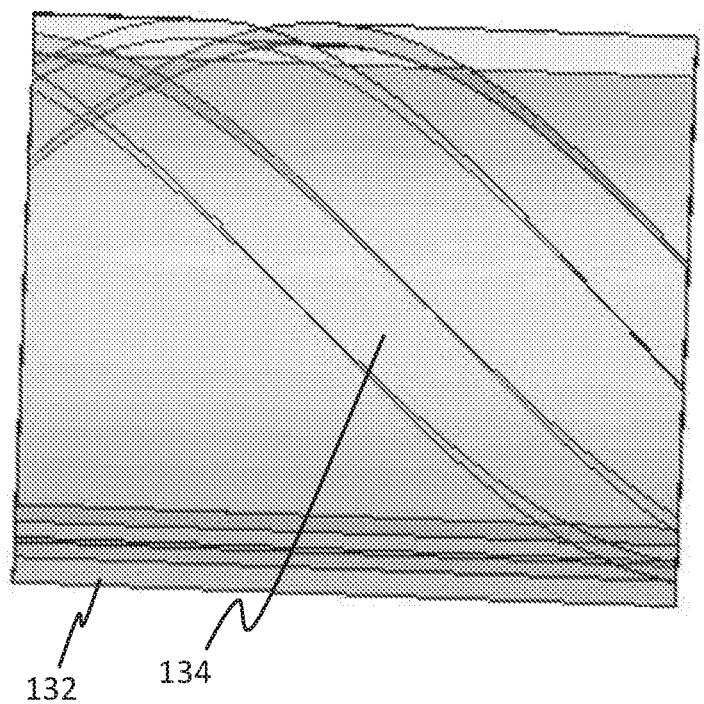
FIG. 9B is a dose selector cam sleeve according to one embodiment.
Figure 9C:
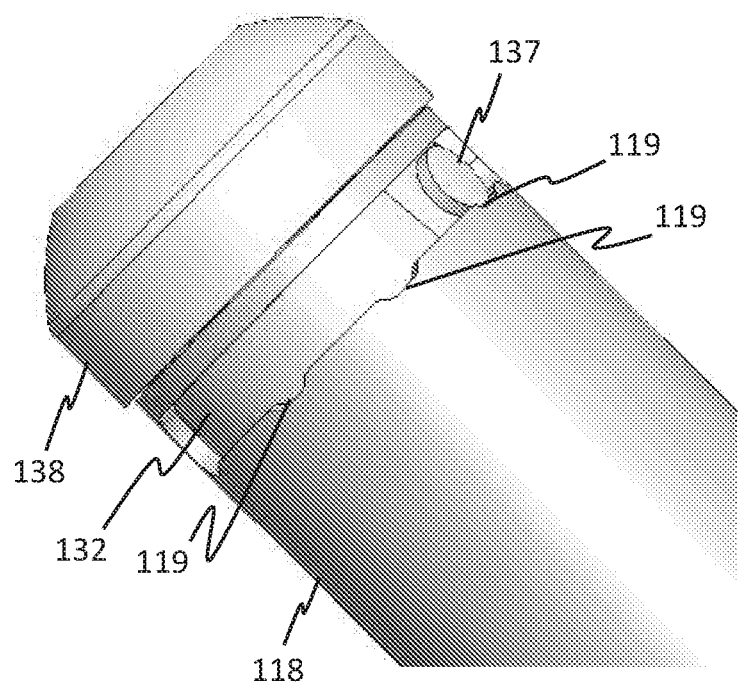
FIG. 9C is a magnified side view of dosage selection components on a partially assembled driver assembly according to one embodiment.
Figure 9D:
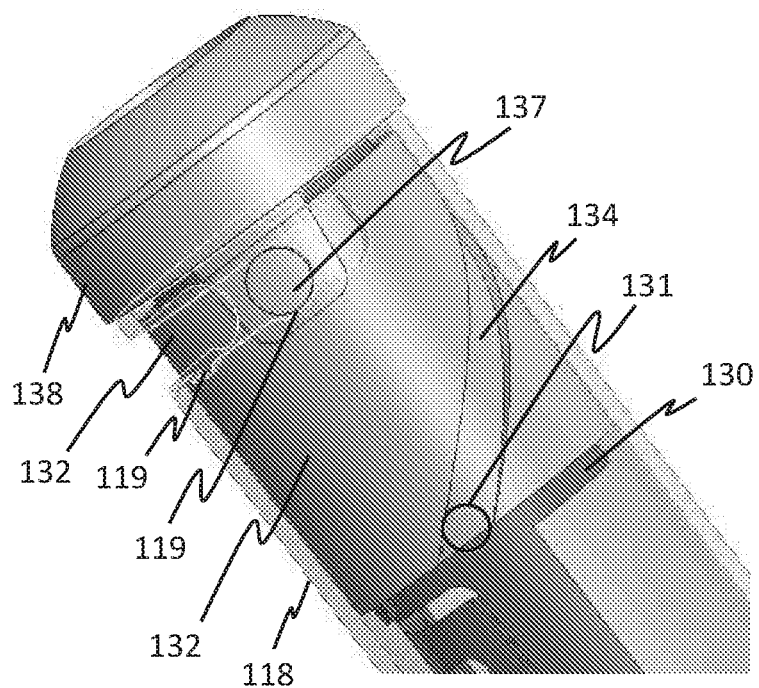
FIG. 9D is a magnified side view of dosage selection components on a partially assembled driver assembly (the chassis is transparent for illustrative purposes) according to one embodiment.

With reference to FIGS. 8A and 8B, the spring assembly 170 includes a reservoir spring button 176 that at least partially houses the reservoir spring 174 and the reservoir spring piston 172. The reservoir spring 174 is configured to exert a constant force on the reservoir spring piston 174 when the spring assembly 170 is assembled with the rest of the device 100.

With reference back to the spring assembly 170 as shown in FIGS. 5A and 5B, the reservoir spring 174 exerts a constant force on the reservoir 157, so that bulk dry powder stored in the reservoir cavity 158 stays pressed up against the distal ends of the inner and outer airway elements 142, 150. When the reservoir spring button 176 is depressed, the spring assembly 170 ejects, allowing the airway assembly to slide out for servicing or replacement.

With reference now to FIGS. 9A-9D, the dose selection mechanism is explained in more detail. The dose selector ring 138 is connected to the dose selector cam sleeve 132, which coaxially surrounds the reservoir driver 130. The reservoir driver has a protrusion 131 that fits into a curved groove 134 in the dose selector cam sleeve 132. The protrusion 131 can move up the curved groove 134 until it reaches the top of the groove and stops. Since the reservoir 157 is connected to the reservoir driver 130, the movement of the reservoir 157 initiated by the dose selector ring 138, while the range of movement of the dose selector ring is limited by the position of the dose selector cam sleeve 132. The dose selector ring 138 can be rotated to various positions to advance the protrusion 131 further up the curved groove 134, effectively manipulating how far the reservoir 157 will move proximally during each twist of the dose selector ring 138. As shown with specific reference to FIGS. 9C and 9D (with body cover 112 removed for illustrative purposes), the chassis 118 has a number of locking indents 119 for holding a protrusion 137 connected to the dose selector ring 138.

In one embodiment, the locking indents are spaced apart to limit the spin of the dose selector cam sleeve 132 in 45 degree intervals, which is equivalent to one dose. Thus, for example, if a particular position limits the spin of the selector cam sleeve 132 to 90 degrees, the proximal movement of the reservoir 157 will equate to shaving off 2 dosages worth of dry powder into the device airways for user inhalation.

A method 200 for dispensing dry powder into an airway of a dry powder inhaler is also shown in FIG. 10, according to one embodiment. A bulk amount of dry powder is stored in a reservoir at step 202. The reservoir is moved towards the airway head at step 204. This can happen by keeping the airway head stationary and moving the reservoir, keeping the reservoir stationary and moving the airway head, or by moving the airway head and reservoir towards each other simultaneously. The relative movement of the reservoir and airway head can be limited to control dosage amounts at step 206. As the airway head contacts the bulk dry powder, a portion of the bulk dry powder is shaved off into an airway of the dry powder inhaler at step 208. During inhalation at step 210, a vortex can be generated within airways of the dry powder inhaler to aerosolize the dry powder at step 212. The vorticial (that is, vortex) airflow can be converted to a dampened and/or laminar airflow for inhalation by the user at step 214.

Advantageously, embodiments of the invention described herein can dispense a measured yet customizable amount of dry powder prior to each inhalation. Further, the inhaler may be capable of storing dry powder in a bulk storage reservoir, in a design that allows for controlled dosages. This functionality is achieved in a reliable mechanism that features a low profile and discrete design. In addition, the dry powder inhaler creates an efficient vorticial (that is, vortex) airflow, such that increased amounts of powder can be picked up into the airway. The airflow can be subsequently converted to a dampened and/or laminar airflow for user inhalation.

The disclosures of each and every patent, patent application, and publication cited herein are hereby incorporated herein by reference in their entirety. As would be understood by those having ordinary skill in the art, the geometries of many of the components can be altered without changing the fundamental purpose and function of the component. While this invention has been disclosed with reference to specific embodiments, it is apparent that other embodiments and variations of this invention may be devised by others skilled in the art without departing from the true spirit and scope of the invention.

The invention claimed is:

1. A dry powder inhaler comprising:
   an elongate body comprising a proximal end, a distal end and an air inlet disposed therebetween;
   a reservoir comprising a reservoir cavity;
   an airway assembly at least partially housed within the body, the airway assembly comprising a first airway, the airway assembly comprises an inner airway element and an outer airway element, the outer airway element at least partially surrounding the inner airway element, wherein the inner airway element comprises at least one curved fin that protrudes into the outer element airway;
   a mouthpiece comprising a mouthpiece airway that is connected to the first airway;
   an airway head attached to the airway assembly that extends into the reservoir cavity; and
   at least one airway assembly opening in the airway assembly connecting the reservoir cavity to the first airway.

2. The dry powder inhaler of claim 1, wherein the inner airway element comprises an inner element airway, the outer airway element comprises an outer element airway, and the inner airway element comprises at least one airway passage to connect the inner element airway to the outer element airway.

3. The dry powder inhaler of claim 2, wherein the outer airway element comprises at least one wall opening for connecting the outer element airway to the air inlet.

4. The dry powder inhaler of claim 1, wherein the at least one curved fin comprises a plurality of curved fins that protrude into the outer element airway.

5. The dry powder inhaler of claim 1, wherein the at least one airway assembly opening is proximal of the airway head.

6. The dry powder inhaler of claim 5, wherein the at least one airway assembly opening comprises a first and second airway assembly opening proximal to the airway head.

7. The dry powder inhaler of claim 1, further comprising:
   a reservoir spring positioned distal of the reservoir and configured to bias the reservoir in a proximal direction.

8. The dry powder inhaler of claim 7 further comprising:
   a dose selector cam sleeve comprising a curved groove that is configured to limit movement of the reservoir.

9. The dry powder inhaler of claim 8, wherein the movement is limited when an element is rotated.

10. The dry powder inhaler of claim 9 further comprising:
    a dose selector ring connected to the dose selector cam sleeve that is configured to limit the rotational movement of the dose selector cam sleeve.

11. The dry powder inhaler of claim 10 further comprising:
    a chassis comprising a plurality of indentations to lock the dose selector ring in a plurality of positions.

12. The dry powder inhaler of claim 1, wherein the mouthpiece is configured to retract distally into a mouthpiece opening disposed in a proximal end of the body.

13. The dry powder inhaler of claim 12, wherein the airway assembly comprises a plug that at least partially blocks the at least one airway assembly opening when the mouthpiece is fully retracted distally.

14. The dry powder inhaler of claim 2, wherein the at least one airway assembly opening is proximal of the airway head.

15. The dry powder inhaler of claim 3, wherein the at least one airway assembly opening is proximal of the airway head.

16. The dry powder inhaler of claim 4, wherein the at least one airway assembly opening is proximal of the airway head.

17. The dry powder inhaler of claim 2, further comprising:
    a reservoir spring positioned distal of the reservoir and configured to bias the reservoir in a proximal direction.

18. The dry powder inhaler of claim 3, further comprising:
    a reservoir spring positioned distal of the reservoir and configured to bias the reservoir in a proximal direction.

19. The dry powder inhaler of claim 4, further comprising:
    a reservoir spring positioned distal of the reservoir and configured to bias the reservoir in a proximal direction.

20. The dry powder inhaler of claim 2, wherein the mouthpiece is configured to retract distally into a mouthpiece opening disposed in a proximal end of the body.

* * * * *